United States Patent [19]

Chen

[11] 3,936,353

[45] Feb. 3, 1976

[54] CONVERSION OF CARBOHYDRATE MATERIALS TO PETROLEUM TYPE HYDROCARBONS

[75] Inventor: Nai Yuen Chen, Titusville, N.J.

[73] Assignee: Mobil Oil Corporation, New York, N.Y.

[22] Filed: Dec. 20, 1974

[21] Appl. No.: 535,008

[52] U.S. Cl. .................. 195/37; 195/32; 195/104; 260/668 R
[51] Int. Cl.² .................. C12C 11/00; C07C 15/02
[58] Field of Search ................ 195/32, 37, 104; 260/668 R; 423/328

[56] References Cited
UNITED STATES PATENTS

| | | | |
|---|---|---|---|
| 3,402,103 | 9/1968 | Amberg et al. | 195/32 |
| 3,493,518 | 2/1970 | Jonassen et al. | 423/328 |
| 3,640,846 | 2/1972 | Johnson | 195/104 |
| 3,780,127 | 12/1973 | Young et al. | 260/688 R |

*Primary Examiner*—Alvin E. Tanenholtz
*Attorney, Agent, or Firm*—Charles A. Huggett; Michael G. Gilman

[57] ABSTRACT

Microbial conversion of agricultural carbohydrate materials to alcohols followed by direct conversion of the oxygenated microbial reaction product to a hydrocarbon product comprising a substantial highly aromatic fraction which is liquid at normal temperatures and pressures. This latter conversion is carried out in the effective presence of a high silica to alumina ratio zeolite like ZSM-5.

3 Claims, No Drawings

3,936,353

CONVERSION OF CARBOHYDRATE MATERIALS TO PETROLEUM TYPE HYDROCARBONS

This invention relates to the production of synthetic petroleum type hydrocarbons. It more particularly refers to the conversion of carbohydrates to hydrocarbons.

The fermentation of sugar to alcohol is many thousands of years old. It is almost equally as old to first convert carbohydrates to sugars and then to convert the sugars to alcohol. This procedure makes excellent alcohol in terms of taste but it is expensive. A large part of the expense involved is in the concentrations stage, that is, the portion of the process in which the fermentation produced alcohol is separated from the water byproduct.

In conventional production of alcohols by fermentation, the fermenter mash is usually subjected to rather extensive distillation in order to recover as much of the produced alcohol as possible in as concentrated a form as possible. Since this mash has a water content which is usually higher than its alcohol content, this distillation step is extensive and expensive and is in fact the heart of alcohol production in a "distillery." Thus distillery produced alcohol is generally too expensive to be used as a chemical intermediate and is usually sold only for drinking and medicinal purposes, which uses can support the extra costs.

There has recently been discovered a process of converting lower alcohols or other similar heteroatom containing organic compounds to highly aromatic hydrocarbon compositions which predominate in the gasoline boiling range, that is have an atmospheric pressure boiling point of up to about 400° to 430°F. Applications Serial Nos. 387,222, now U.S. Pat. No. 3,894,106, 387,223 now U.S. Pat. No. 3,894,107, and 387,224, now U.S. Pat. No. 3,907,915 all filed Aug. 9, 1973, are directed to this conversion. Since gasoline is a relatively cheap commodity when derived from petroleum oil, it has been very difficult in the past to develop processes to convert non-petroleum raw materials to gasoline boiling range hydrocarbons of appropriate gasoline quality. In fact, the governments of some countries around the world have, at various times, legislated the inclusion of grain alcohol is "gasoline" compositions as a means of supporting the local grain industry. This indicates that alcohol is too inherently expensive to be used as a gasoline fuel in the free marketplace. However, with the development of the new alcohol conversion technology referred to above, and the recent worldwide increases in the cost of crude oil, the economic incentives for converting alcohol to gasoline have improved.

It is an object of this invention to provide an improved process for converting alcohol to gasoline.

It is another object of this invention to provide improved means of converting natural materials, such as grain, to gasoline.

It is a further object of this invention to improve the economics of inclusion of cellulose and/or sugar derived alcohol into gasoline.

Other and additional objects of this invention will become apparent from a consideration of this entire specification including the claims hereof.

In accord with and fulfilling these objects, one aspect of this invention resides in the process of: microbially converting carbohydrates and/or cellulosics to an oxygenated lower aliphatic organic compound product comprising ethanol and water in a conventional manner; directly, and without intermediate separation of all of the water from the organic components of this product, converting the liquid portion of this product at a temperature of about 500° to 1000°F in effective contact with a crystalline aluminosilicate zeolite having a silica to alumina ratio of at least 12 and a constraint index of 1 to 12; and then recovering at least the liquid hydrocarbon portion of the product of this conversion. This last separation is suitably by decantation thus reducing the energy consumption of the overall process as compared to separation of the ethanol and water by fractionation.

The class of zeolites utilized in this invention has some unusual properties. These zeolites by themselves induce profound transformations of aliphatic hydrocarbons to aromatic hydrocarbons in commercially desirable yields. Although they have unusually low alumina contents, i.e., high silica to alumina ratios, they are very active even when the silica to alumina ratio exceeds 30. The activity is surprising since the alumina in the zeolite framework is believed responsible for catalytic activity. They retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity.

An important characteristic of the crystal structure of this class of zeolites is that it provides constrained access to, and egress from this intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic form within the channels. Although zeolites with a silica to alumina ratio of at least 12 are useful, it is preferred to use zeolites having higher ratios of at least about 30. Such zeolites after activation, acquire an intracrystalline sorption capacity for normal hexane which is greater than that for water, i.e., they exhibit "hydrophobic properties". It is believed that this hydrophobic character is advantageous in the present invention.

The type zeolite useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight membered rings of oxygen atoms, then access to molecules of larger cross-section than normal hexane is excluded and the zeolite is not of the desired type. Windows of ten-membered rings are preferred, although excessive puckering or pore blockage may render these zeolites ineffective. Twelve-membered rings do not generally appear to offer sufficient constraint to produce the advantageous conversions, although structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of equal weight of normal hexane and 3-methylpentane over a small sample, approximately 1 gram or less, of zeolite at atmospheric pressure according to the folllowing procedure. A sample of the zeolite, in the form of pellets or extrudate, is crushed to a particle size about that of coarse sand and mounted in a glass tube. Prior to testing, the zeolite is treated with a stream of air at 1000°F for at least 15 minutes. The zeolite is then flushed with helium and the temperature adjusted between 550°F and 950°F to give an overall conversion between 10% and 60%. The mixture of hydrocarbons is passed at 1 liquid hourly space velocity (i.e. 1 volume of hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for use as catalyst for the present invention are those having a constraint index from 1.0 to 12.0, preferably 2.0 to 7.0.

The class of zeolites defined herein is exemplified by ZSM-5 type including ZSM-11, ZSM-21 and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated hereby reference.

ZSM-21 is more particularly described in U.S. application, Ser. No. 358,192, filed May 7, 1973, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000°F for one hour, for example, followed by base exchange with ammonium salts followed by calcination at 1000°F in air. The presence of organic cations in the forming solution may not be absolutely essential to the formation of this type zeolite; however, the presence of these cations does appear to favor the formation of this special type of zeolite. More generally, it is desirable to activate this type zeolite by base exchange with ammonium salts followed by calcination in air at about 1000°F for from about 15 minutes to about 24 hours.

Natural zeolites may sometimes be converted to this type zeolite by various activation procedures and other treatments such as base exchange, steaming, alumina extraction and calcination, in combinations. Natural minerals which may be so treated include ferrierite, brewsterite, stillbite, dachiardite, epistilbite, heulandite, and clinoptilolite. The preferred crystalline aluminosilicates are ZSM-5, ZSM-11 and ZSM-21 with ZSM-5 particularly preferred.

In a preferred aspect, zeolites used herein are selected as those having a crystal density, in the dry hydrogen form, of not substantially below about 1.6 grams per cubic centimeter. It has been found that zeolites which satisfy all three of these criteria are most desired. Therefore, the preferred catalysts of this invention utilize zeolites having a constraint index as defined above of about 1 to 12, a silica to alumina ratio of at least about 12 and a dried crystal density of not less than about 16 grams per cubic centimeter. The dry density for known structures may be calculated from the number of silicon plus aluminum atoms per 1000 cubic Angstroms, as given, e.g. on page 11 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

One aspect of this invention resides in the novel use of carbohydrates as raw materials for the production of higher hydrocarbons, particularly gasoline boiling range, highly aromatic hydrocarbon mixtures. These carbohydrates include sugars, starches and cellulosics, i.e. all vegetation and algae. Carbohydrates can be considered to be composed of carbon and water. Therefore, decarboxylation of carbohydrates, in rejecting carbon and oxygen, leaves oxygenated hydrocarbons behind. This is the crux of the process of fermentation of grains to ethanol. It is carried out at low temperatures and is mildly exothermic. It is well suited to be carried out in a water medium which eliminates the need for removing water from the vegetation prior to conversion thereof into alcohol. This fermentation reaction is, as above-noted, well known and has been widely practiced for thousands of years.

Conventionally, the fermentation product is a very dilute aqueous solution of alcohol. It is conventional that this solution also has admixed with it solid fermentation residue and various inorganic nutrients. Conventionally, the "mash" is subjected to fractional distillation of concentrate and purify the alcoholic solution as well as separate it from the solid portion of the mash. This fractional distillation removes very large quantities of water and is the most expensive and energy consuming step in the process of making alcoholic liquor.

The crux of the instant invention is, however, based upon the fact that the particular zeolite catalysts used herein to convert the alcohol to aromatic hydrocarbon gasoline are not particularly sensitive to water or to the other components of the mash under the conditions which are useful for this conversion. The fact is that alcohol has a higher vapor pressure than water and can, therefore, be inexpensively separated from the fermented mash in a stripping column if the purity and anhydrousness of the alcohol is not critical. Unlike a fractionation column, which is needed to separate a concentrated purified alcohol solution from the mash, the energy consumption of a stripping column is relatively small because the distillate overhead does not need to be condensed and recycled (refluxed), i.e. operating with a high reflux ratio in order to increase the efficiency of separation. The stripping column can be of any conventional design such as a packed tower or a bubble-plate column. The fermenter mash, suitably after being separated from its solid components, is preheated in a conventional heat exchanger and fed to the top of the column. In the production of ethyl alcohol, the fermenter mash suitably contains between 6 and 12% ethyl alcohol, the vapor in equilibrium with this liquid suitably containing 39 to 54% ethyl alcohol. Heat is supplied at the bottom of the column removing the last trace of ethyl alcohol from the liquid.

It is appropriate that the mash distillate (that is the stripper overhead) contain about 40 to 70 weight per cent water. Preferred water content is about 50%. This highly aqueous solution of alcohol is then converted to gasoline over a suitable zeolite catalyst as aforesaid. Not only is the water which is carried through the alcohol conversion reaction not detrimental to this reaction and its catalyst, but it actually serves a most useful purpose. The conversion of alcohols to gasoline boiling range hydrocarbons is quite exothermic and must be cooled to a substantial extent to keep the reaction from running away out of control. The large amount of water fed to the conversion reaction as well as the large amount of water made in the conversion reaction act as a heat sink for the heat generated in the alcohol conversion.

One of the advantages of the instant invention over the prior art technology is in the amount of energy required to carry out the process. The reason for the big difference in the amount of energy required is because of the high temperatures required in the prior art technology. This will become clear when we examine the similarities and differences between prior art technology and the process of the instant invention.

From an overall reaction point of view, all the processes including the instant invention of converting carbohydrates to motor fuel are the same, i.e. they may be described as a process of decarboxylation and dehydration of carbohydrates to produce a hydrocarbon mixture with $CO_2$ and $H_2O$ as byproducts. The overall reaction may be written as follows:

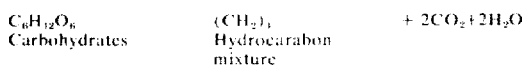

However, to carry out this reaction in a practical scheme, there are major differences among various processes. In the case of prior art technology, the agricultural or other raw material must first be dried to reduce its moisture content and the initial processing step generally involves a high temperature gasification step, such as high temperature pyrolysis or steam reforming, and a water gas shift reaction or combinations thereof to yield a mixture of carbon monoxide and hydrogen of the desired ratio for further conversion. $CO_2$ is released as a byproduct in this step. After elaborate purification steps, the mixture of CO and $H_2$ is reacted at high pressure and high temperature, for example, in the Fisher-Tropsch synthesis to produce liquid hydrocarbons or alternatively reacted under pressure to produce methanol and then reacting methanol over a crystalline aluminosilicate zeolite catalyst, (see application Ser. No. 387,222, filed Aug. 8, 1973 and other applications referred to therein, to produce liquid hydrocarbons).

In the instant invention, the raw material need not be dried, in fact, additional water may be desirable during processing. The first step generally involves the conversion of the carbohydrates to fermentable sugars, (except, of course, when sugar such as molasses is the raw material). Included in this step are grinding, cooking and hydrolysis, enzymic or acid, all of which are conventional and conducted at temperatures not much above the boiling point of water. Examples of enzymic hydrolysis process for starchy raw materials, e.g., grains, potatoes, etc. include the use of barley-malt amylases and Fungal amylases. The latter can be produced by the use of microorganisms of the genera Rhizopus and Asperigillus. For cellulosic raw materials, Fungi of the genera Trichoderma, Irpex, Myrothecium and Bacteria of the genus Cellvibrio can be used. Acid hydrolysis is usually carried out in the presence of a dilute inorganic acid solution such as hydrochloric acid. Following hydrolysis, the fermentable sugar solution is innoculated with a yeast culture, and the conversion of sugar to ethanol take place anaerobically at room temperature (60°–90°F) and atmospheric pressures. $CO_2$ is released as a byproduct in this step. After fermentation, the fermenter mash is stripped of its alcohol and converted to hydrocarbons as described above.

To further quantify the difference in the amount of energy required to carry out the process, a reasonable and direct comparison may be made between a process converting glucose to methanol and the instant invention, part of which involves the conversion of glucose to a 50% ethanol solution, since the energy required for the following step converting the alcohols to hydrocarbons is similar for both processes.

The major energy demanding steps (including evaporation and heat of reaction only) for the methanol synthesis process may be listed as follows:

|  | Btu/lb. carbon in glucose |
|---|---|
| Removal of moisture from raw material (endothermic) | 5,750 |
| Steam reforming (endothermic) | 3,500 |
| Water gas shift (exothermic) | 485 |
| Methanol synthesis (exothermic) | 2,177 |
| Total | 11,912 |

It is noted that the individual steps in the prior art technology are all either high exothermic or highly endothermic and the sum of the energy demand represents approximately 85% of the heating value of the carbon content of the feed. Thus, in order to improve the thermal efficiency of converting the energy stored in carbohydrates to energy in liquid hydrocarbon fuel, expensive investment in heat transferring equipment, such as boilers, heat exchangers, recycle compressors, specialized reactors, etc. must be used, and most of which must withstand both high temperatures and high pressures.

The major energy demand step for producing a 50% aqueous ethanol solution by the instant invention may be listed as follows:

|  | Btu/lb. carbon in sugars |
|---|---|
| Fermentation (exothermic) | 560 |
| Stripping (endothermic) | 1,700 |
|  | Total 2,260 Btu/lb. Carbon in glucose |

It is noted that many of the highly endothermic and exothermic reaction steps in the prior art technology are now combined and the combined reaction is only mildly exothermic. Furthermore, by eliminating the necessity of producing pure ethanol as a product, the energy required to separate ethanol from the fermenter mash is not large. Thus, the inherent thermal efficiency will be high. Since the process is preferably carried out at about atmospheric pressure and only slightly above the boiling point of water, expensive heat transfering equipment will not be required.

It is interesting to note that the hydrocarbon yield from green vegetation according to this invention is about 9 weight percent based upon the total harvested weight of the vegetation. This equates quite nicely to the yield from oil bearing shale and is substantially less ecologically destructive. Further, while hydrocarbon fuels from shale or crude oil or coal are a resource which will eventually at some future time be completely depleted, hydrocarbons produced by the instant process are continually renewed; the hydrocarbons produced are burned to make carbon dioxide and water which the plants then reconvert to carbohydrates which are harvested and converted as set forth herein thus producing a truly cyclical process.

What is claimed is:

1. In the process of converting carbohydrates to gasoline boiling range hydrocarbons comprising fermenting said carbohydrates to an intermediate product comprising water, alcohol and solid fermentation products; distilling the alcohol from said intermediate product; and converting said alcohol to said hydrocarbons by contacting such with a crystalline aluminosilicate zeolite catalyst having a silica to alumina ratio of at least 12 and a constraint index of about 1 to 12 at about 500° to 1000°F; the improvement which comprises instead of distilling said intermediate product, flashing said intermediate product to remove a distillate of alcohol and about 40 to 70 weight percent water therefrom; and directly contacting said water-alcohol distillate from said flashing with said zeolite at said temperature.

2. The improved process claimed in claim 1 including stripping the fermenter mash to a distillate of about half water, half alcohol.

3. The improved process claimed in claim 1 wherein said zeolite is a ZSM-5.

* * * * *